(12) United States Patent
Kato et al.

(10) Patent No.: US 6,992,196 B2
(45) Date of Patent: Jan. 31, 2006

(54) METHOD FOR PRODUCING REFINED ETHYLENE SULFITE

(75) Inventors: Toshimitsu Kato, Mie (JP); Norioki Mine, Mie (JP); Minoru Kotato, Ibaraki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 298 days.

(21) Appl. No.: 10/227,242

(22) Filed: Aug. 26, 2002

(65) Prior Publication Data

US 2003/0049542 A1    Mar. 13, 2003

(30) Foreign Application Priority Data

Aug. 29, 2001 (JP) ............................ 2001-259262

(51) Int. Cl.
C07D 327/10 (2006.01)
C07D 343/00 (2006.01)
C07D 411/00 (2006.01)

(52) U.S. Cl. ...................................... 549/34
(58) Field of Classification Search .................. 549/34
See application file for complete search history.

(56) References Cited

FOREIGN PATENT DOCUMENTS

GB          346685      * 11/1929

OTHER PUBLICATIONS

Carlson et al., Hydroxyalkylation with Cyclic Alkylene Esters. I. Synthesis of Hydroxyethylapocupreine, J. Am. Chem. Soc., 69 1952 (1947).*
Malima et al., Action of Thionyl Chloride upon Polyatomic Alcohols, Proc. Imp. Acad (Japan), 1926, 2, 544-546.*
Multi-Sulfur and Sulfur and Oxygen Five-and Six-Membered Heterocycles, In Two Parts, Part One, The chemistry of Heterocyclic Compounds, First published 1966 by John Wiley & Sons, Ltd.
Synthesis of Biocidal Agent of Quaternary Ammonium Intramolecular Salt Type, Jul. 8, 1994.

* cited by examiner

Primary Examiner—Johann Richter
Assistant Examiner—Chukwuma Nwaonicha
(74) Attorney, Agent, or Firm—Manabu Kanesaka

(57) ABSTRACT

Refined ethylene sulfite exhibits an excellent storage stability when used as a constituent of an electrolyte. A method of producing same has a step of reacting ethylene glycol and thionyl chloride to producing raw ethylene sulfite, a rectifying step for rectifying the raw ethylene sulfite, and a refining process for refining the raw ethylene sulfite or the rectified ethylene sulfite conducted before or after the rectifying step. The refining process is at least one process selected from the group consisting of a washing process, a dehydration process by total reflux distillation, a second rectifying process, and an absorbing process. Refined ethylene sulfite produced according to the method contains chloroethanol in an amount of not more than 1000 ppm.

6 Claims, No Drawings

METHOD FOR PRODUCING REFINED ETHYLENE SULFITE

BACKGROUND OF THE INVENTION

The present invention relates to a method for producing ethylene sulfite or refined ethylene sulfite which is useful for an application to an electrolyte.

Ethylene sulfite is used as a raw material in various fields of organic synthesis, and a solvent or an additive for an electrolyte of a lithium secondary battery or the like.

Examples of conventional methods for producing the ethylene sulfite are:
i) a method of reacting ethylene glycol and thionyl chloride;
ii) a method of reacting ethylene glycol and dimethyl sulfite;
iii) a method of reacting ethylene oxide and sulfur dioxide;
iv) a method of depolymerizing polyethylene sulfite Among these methods, the method of reacting ethylene glycol and thionyl chloride has been considered advantageous industrially due to safety and low costs.

D. S. Bleslow and H. Skolnic, Chem. Heterocycl. Compound., 1966, 21-1,1 describes the method of reacting ethylene glycol and thionyl chloride for producing ethylene sulfite without solvent and catalyst.

However, ethylene sulfite produced by the above conventional methods contains a large amount of impurities.

The ethylene sulfite produced by the conventional methods is unsuitable for a solvent and an additive for an electrolyte for a lithium secondary battery, since the ethylene sulfite contains impurities so much that the electrolyte does not have good storage stability. For example, the electrolyte containing the ethylene sulfite produced by the conventional methods tends to cause an increase of acid content during preservation. When the electrolyte is used for a lithium secondary battery, the battery is increased in its internal pressure due to the electrolyte which sometimes damages a canister of the battery.

Thus, there has been required ethylene sulfite having high purity in order to improve performance of the battery.

SUMMARY OF THE INVENTION

It is an object of the present invention to overcome aforementioned problems and provide a method of producing the ethylene sulfite.

Ethylene sulfite of the invention is produced by reacting ethylene glycol with thionyl chloride, and the ethylene sulfite contains chloroethanol in an amount of not more than 1000 ppm.

A method of the invention is for refining raw ethylene sulfite which is obtained by reacting ethylene glycol with thionyl chloride by a process including a rectification process A, wherein the method further has at least one purification process which is conducted before or after the rectification process A, and which is selected from the group consisting of a washing process with basic water, a dehydration process by refluxing, a distillation (rectification B) process, and an absorption process.

An electrolyte of the invention for a lithium battery consists of ethylene sulfite, wherein the ethylene sulfite contains chloroethanol in an amount of not more than 1000 ppm.

A lithium battery of the invention has an electrolyte, wherein the electrolyte contains ethylene sulfite containing chloroethanol in an amount of not more than 1000 ppm.

DETAILED DESCRIPTION

A chlorine content in the ethylene sulfite is found to have an influence to the storage stability of the electrolyte, and that chloroethanol contained in the ethylene sulfite significantly influences the storage stability of the electrolyte and stability of the lithium secondary battery containing the electrolyte.

The refined ethylene sulfite can be produced by producing the raw or crude ethylene sulfite by reacting ethylene glycol and thionyl chloride, and rectifying the crude ethylene sulfite to produce refined ethylene sulfite.

<Production Method of the Raw Ethylene Sulfite>

Reaction of ethylene glycol and thionyl chloride to produce the raw or crude ethylene sulfite can be conducted either with or without a solvent and/or catalyst.

Examples of the solvent are: hydrocarbon halogenides such as methylene chloride; esters such as ethyl acetate; nitrites such as acetonitrile; ethers such as tetrahydrofuran and dimethoxyethane; and aromatic hydrocarbons such as toluene, but the solvent is not limitative thereto.

The catalyst may be at least one basic compound, and examples thereof are inorganic bases such as sodium carbonate, potassium carbonate, sodium hydroxide, potassium hydroxide and calcium hydroxide, and organic bases such as N-methyl piperidine and N-ethyl morpholine.

Reaction temperature can be in a range of −20 to 100° C., preferably of 0 to 80° C. Reaction time can be in a range of 0.5 to 10 hours, preferably of 0.5 to 5 hours.

When the reaction product contains the solvent(s), the raw ethylene sulfite can be produced by distilling the reaction product. The raw ethylene sulfite also contains unreacted ethylene glycol, by-produced chloroethanol, and other impurities. The raw ethylene sulfite contains salt(s) of a basic compound and hydrogen chloride when the reaction process employs a catalyst of the basic compound. The salt can be removed from the raw ethylene sulfite by filtration, washing or rinsing, extraction and so on.

<Refining the Raw Ethylene Sulfite>

Raw ethylene sulfite which is obtained by reacting ethylene glycol with thionyl chloride is refined by a process including a rectification process A, and by at least one purification process selected from the group consisting of a washing process with basic water, a dehydration process by refluxing, a distillation (rectification B) process, and an absorption process which is conducted before or after the rectification process A.

<Simple Distillation Process>

The simple distillation process can be conducted under either normal pressure or reduced pressure, and can be conducted at an internal temperature not higher than 100° C.

<Rectifying Processes (Rectification A and Rectification B)>

The rectifying process (rectification A and rectification B) can be conducted with a rectifying column normally having theoretical plates of 2 to 15 preferably 3 to 10 under either normal or reduced pressure, preferably at an internal temperature not higher than 100° C., and at a reflux ratio of about 3 to 15.

The rectification A and the rectification B may be conducted under either the same condition or different conditions.

<Washing Process with Basic Water>

The washing process can be conducted with water or a basic water dissolved therein a basic inorganic salt such as sodium hydrogen carbonate, and is continued until the water phase becomes neutral. In this washing process, the amount of washing water or the number of application is not limitative.

<Dehydration Process by Total Reflux Distillation>

The process is conducted at an internal temperature not higher than 100° C. and at a pressure not higher than 20 Torr, so as to discharge water out of the system in the form of non-condensed gas. The time of processing can be normally in a range of 1 to 5 hours.

<Absorption Process>

The absorption process employs an absorbent which may be complex metal oxide such as molecular sieves, activated carbon, or metal oxide such as aluminum oxide ($Al_2O_3$) and magnesium oxide (MgO). The amount of the absorbent can be 10% or less to the ethylene sulfite, but is not limitative thereto. The process can be either a batch or a continuous process.

<Combination of Refining Process>

The raw ethylene sulfite is refined preferably by the simple distillation, the first rectifying process and at least one refining process, wherein the refining process can be conducted either before or after the first rectifying process. Combinations of the first rectifying process and the refining process(es) include the absorbing process and the rectifying process; the washing process, the dehydration process by total reflux distillation and the rectifying process: and the washing process, the dehydration process by total reflux distillation, the absorbing process and the rectifying process.

The above method provides the refined ethylene sulfite. The refined ethylene sulfite contains chlorine in an amount not more than 500 ppm, preferably not more than 200 ppm, and also contains chloroethanol in an amount not more than 1000 ppm, preferably not more than 400 ppm.

<Determination of Total Chlorine Content in Ethylene Sulfite>

A sample is diluted with an inert solvent for ethylene sulfite (for example, toluene) and is burned in an oxyhydrogen flame combustor. The resulted product is absorbed in a water solution of hydrogen peroxide. Chlorine ion content in the water solution is determined by ion chromatography, and the total chlorine content is calculated.

<Determination of Contents of Ethylene Sulfite, Chloroethanol and Ethylene Glycol>

A sample is diluted by an inert solvent for ethylene sulfite (for example, toluene) and is subjected to a gas chromatograph (column: dimethyl polysiloxane type, detector: Flame Ionizaion Detector (FID)). The contents of ethylene sulfite, chloroethanol and ethylene glycol are expressed in percentage by area respectively.

The ethylene sulfite containing not more than 1000 ppm chloroethanol according to the embodiment is useful for a solvent and an additive of the electrolyte for the lithium battery, especially for the lithium secondary battery.

The electrolyte for a lithium battery according to another aspect of the invention contains at least one lithium electrolyte, at least one solvent, and ethylene sulfite containing not more than 1000 ppm chloroethanol. The ethylene sulfite containing not more than 1000 ppm chloroethanol can be prepared according to the above-described method. The lithium electrolyte may be a lithium compound such as lithium borofluoride, lithium phosphate hexafluoride, lithium perchlorate, and lithium trifluoromethanesulfonate. The solvent may be a usual one for an electrolyte such as a cyclic carbonate including ethylene carbonate and propylene carbonate; a chane carbonate including dimethyl carbonate and methyl ethyl carbonate; an ether group including tetrahydrofuran and 1,2-diethoxyethane; and a lactone group such as γ-butyrolactone. The ethylene sulfite containing not more than 1000 ppm chloroethanol can be used for either the solvent or the additive. The ethylene sulfite having the reduced amount of chloroethanol has a good storage stability, and the acid content therein can be kept low for a long time of storage, so that it is useful for the electrolyte for the lithium battery especially for the lithium secondary battery. On the other hand, the electrolyte consisting of ethylene sulfite containing more than 1000 ppm chloroethanol has an inferior storage stability.

<Determination of Acid Content in Electrolyte>

A precisely weighed sample is dissolved in cold pure water, and then the water is titrated by alkali where the indicator is BTB(bromothymol blue) changing yellow to blue. The amount of the titrant is converted to the acid content expressed as hydrofluoric acid content.

The ethylene sulfite refined through the above processes is normally reduced in content of unreacted ethylene glycol to 2000 ppm or less, so that it is also useful for the solvent and the additive for the electrolyte of the battery, preferably the secondly battery.

EXAMPLES AND COMPARATIVE EXAMPLES

Without further elaboration, it is believed that one skilled in the art, using the preceding description, can utilize the present invention to its fullest extent. The following embodiments are, therefore, to be construed as merely illustrative, and not limitative in any way whatsoever, of the remainder of the disclosure.

The present invention is further illustrated by the following Examples and Comparative Examples. The determination is conducted as follows.

<Determination of Total Chlorine Content in Ethylene Sulfite>

A sample was diluted with toluene and was burned in an oxyhydrogen flame combustor. The resulted product was absorbed in a water solution of 3% hydrogen peroxide. Chlorine ion content in the water solution was determined by ion chromatography, and the total chlorine content was calculated.

<Determination of Contents of Ethylene Sulfite, Chloroethanol and Ethylene Glycol>

A sample was diluted by toluene and was subjected to a gas chromatograph (GC 14A manufactured by Shimadzu Corporation having a column of HR-1) in such a manner that the temperature was held at 80° C. for 5 minutes and then raised to 220° C. at a rate of 8° C./min, and then held for 10 minutes, and an injector and a detector (FID) were kept at 250° C. The contents of ethylene sulfite, chloroethanol and ethylene glycol were expressed in percentage by area respectively, where the limits of detection of chloroethanol and ethylene glycol were both 25 ppm.

<Determination of Acid Content in Electrolyte>

A precisely weighed 10 g sample was dissolved in 100 $cm^3$ pure water of 5° C. or lower, and then the water was titrated by alkali where the indicator was BTB(bromothymol blue) changing yellow to blue. The amount of the titrant was converted to the acid content expressed as hydrofluoric acid content.

<Production(I) of Raw Ethylene Sulfite>

1 kg of ethylene glycol (available from Mitsubishi Chemical Corporation) was held in a flask having a capacity of 2 liters. The flask was evacuated to reduce the internal pressure to 30 Torr at a room temperature, and then nitrogen gas was introduced into the flask to substitute the atmosphere. After that, a total amount of 2.1 kg of thionyl chloride (available from Kishida Chemicals Ltd., purity:95%) was dropped into the flask for 6 hours, while agitating the contents in the flask, through which the internal temperature rose up to 45° C. After finished dropping the thionyl chloride, the contents were aged at an internal temperature of 68° C. for 70 minutes, and then the flask was evacuated to 35 Torr and kept at an internal temperature of 63° C. for 25 minutes. The resulted reaction product was thin-brown liquid containing ethylene sulfite of 97.04%, chloroethanol of 0.47% and ethylene glycol of 1.30%.

The product was simple-distilled at a pressure of 20 Torr with a heat medium having a constant temperature of 85° C. The initial distillate which was 5% of the total distillate was cut off and removed therefrom. The product distillate thus distilled at a yield of 86% was the raw ethylene sulfite which contained ethylene sulfite of 97.7%, chloroethanol of 0.28%, ethylene glycol of 1.6% and total chlorine of 5300 ppm.

It should be noted that the raw ethylene sulfite thus obtained was employed as a starting raw ethylene sulfite in the later-described Examples 1 to 4 respectively as well as the below-described rectifying process, so that the raw ethylene sulfite is sometimes referred to as parent raw ethylene sulfite hereinafter.

The parent raw ethylene sulfite was rectified with a rectifying column having ten theoretical plates and a heat medium having a temperature of 91° C., wherein the reflux ratio was kept at 10 until 5% of the distillate was distilled out initially, and after that, the ratio was kept at 5.

The refined ethylene sulfite distilled at a yield of 71.8%, had a purity of 99.30%, and contained chloroethanol of 0.14%, ethylene glycol of 0.38% and total chlorine of 1600 ppm.

Example 1

The above parent raw ethylene sulfite was subjected to an absorbing treatment with an activated carbon (Sekado BW-50, produced by Shinagawa Chemicals Ltd.) as an absorbent, wherein the activated carbon was added in the raw ethylene sulfite in an amount of 10% and then the ethylene sulfite was agitated for 5 hours. The ethylene sulfite was further rectified in the same manner as the above Production (I).

The ethylene sulfite was rectified at a yield of 68%, and had a purity of 99.5%, and contained chloroethanol of 0.09%, ethylene glycol of 0.18% and total chlorine of 480 ppm.

Example 2

The parent raw ethylene sulfite was added with a sodium hydrogen carbonate saturated solution in an amount of 30% by weight, was agitated for one hour and then left at rest for 30 minutes, and after that, the water phase was removed. After the resultant was added with water in an amount of 20% by weight, it was agitated for one hour. After it was left at rest for 30 minutes, the water phase was removed. The ethylene sulfite thus washed two times was dehydrated by dehydration process by total reflux distillation at an internal temperature of 70° C. and at a pressure of 20 Torr for 5 hours, while discharging water out of the system. The dehydrated ethylene sulfite was further rectified in the same manner as the Production (I).

The ethylene sulfite was rectified at a yield of 60.1%, and contained chloroethanol of 0.09%, ethylene glycol of 0.05% and total chlorine of 110 ppm.

Example 3

The refined ethylene sulfite obtained in Example 2 was further treated by the absorbing treatment with a molecular sieve of 5A as an absorbent, wherein the absorbent was added into the refined ethylene sulfite in an amount of 3%, and then the ethylene sulfite was agitated for 5 hours. After that, the treated ethylene sulfite was rectified in the same manner as the Production (I).

The ethylene sulfite was rectified at a yield of 54%, and contained chloroethanol of 0.01%, ethylene glycol of 0.01% or less and total chlorine of 40 ppm or less.

Example 4

440 kg of ethylene glycol (available from Mitsubishi Chemical Corporation) was held in a reaction vessel having a capacity of 1m3. The vessel was evacuated to reduce the internal pressure to 30 Torr at a room temperature, and then nitrogen gas was introduced into the vessel to substitute the atmosphere. After that, a total of 900 kg of thionyl chloride (available from Kishida Chemicals Ltd., purity: 95%) was dropped into the vessel for 12 hours, while agitating the contents in the vessel, through which the internal temperature rose up to 35° C. Having finished dropping the thionyl chloride, the contents were aged at an internal temperature of 68° C. for 70 minutes, and then the vessel was evacuated to 95 Torr and kept at an internal temperature of 69° C. for 3 hours.

The reaction product was simple-distilled at a pressure of 20 Torr with a heat medium having a constant temperature of 85° C. The initial distillate which was 5% of the total distillate was cut off and removed to obtain the raw ethylene sulfite. The raw ethylene sulfite was added with a sodium hydrogen carbonate saturated solution in an amount of 30% by weight, and was agitated for one hour. After it was left at rest for 30 minutes, the water phase was removed. After the resultant was added with water in an amount of 20% by weight, it was agitated for one hour. After it was left at rest for 30 minutes, the water phase was removed. The ethylene sulfite thus washed two times was dehydrated by dehydration process by total reflux distillation at an internal temperature of 70° C. and at a pressure of 20 Torr for 5 hours, while discharging water out of the system. The dehydrated ethylene sulfite was rectified with a rectifying column having ten theoretical plates and a heat medium having a temperature of 90° C., wherein the reflux ratio was kept at 10 until 5% of the distillate was distilled out initially and after that, the ratio was kept at 5. The refined ethylene sulfite was further treated by the absorbing treatment with a molecular sieve of 5A as an absorbent, wherein the absorbent was added into the refined ethylene sulfite in an amount of 3%, and then the ethylene sulfite was agitated for 5 hours. After that, the treated ethylene sulfite was rectified with the rectifying column having ten theoretical plates and a heat medium having a temperature of 90° C., wherein the reflux ratio was kept at 10 until 5% of the distillate was distilled out initially, and after that, the ratio was kept at 5.

The ethylene sulfite was rectified at a yield of 62%, and contained chloroethanol in an amount below the limit of detection, ethylene glycol in an amount below the limit of detection, and total chlorine of 40 ppm or less.

<Stability of Electrolyte Added with the Above Ethylene Sulfite>

An electrolyte was prepared as follows:

Ethylene carbonate of 286 g and ethylmethyl carbonate of 514 g were mixed. Having been added with a molecular sieve 4A of 5.1 g as an absorbent, the mixture was dehydrated for 5 hours. The mixture was then filtrated by filter of 1 $\mu$m. The filtered mixture was added with commercially available $LiPF_6$ of 114 g little by little, and then stirred for 30 minutes. After that, the mixture was filtrated by a filter of 11 $\mu$m again so as to prepare the electrolyte. The electrolyte contained acid of 9.5 ppm and water of 5.1 ppm.

Five samples i), ii), iii), iv) and v) consisting of the electrolyte were prepared, and each of the samples ii) to iv) was added with ethylene sulfite in an amount of 2 wt % respectively.

To the first sample i), ethylene sulfite was not added.

To the second sample ii), ethylene sulfite which was prepared in Example 3 containing chloroethanol of 0.01% was added.

To the third sample iii), ethylene sulfite which was prepared in Example 3 and further the chloroethanol were added till its concentration in ethylene sulfite became 0.21%.

To the fourth sample iv), ethylene sulfite which was prepared in Example 3 and further added with the chloroethanol till its concentration in ethylene sulfite became 0.35% was added.

To the fifth sample v), ethylene sulfite which was prepared in Example 4 containing chloroethanol in an amount less than 25 ppm which was below the limit of detection was added.

Each of the samples i) to v) of the electrolyte was stocked in a stainless steel (SUS No. 304: American Iron and Steal Institute) container and held at a temperature of 25° C. in an atmosphere of nitrogen. Acid contents of the samples were determined on the first day and after ten days. The results are shown in Table 1.

TABLE 1

| No. of electrolyte | Concentration of chloroethanol in ethylene sulfite | Initial acid content (ppm) | Acid content after 10 days (ppm) |
| --- | --- | --- | --- |
| i) | — (No ethylene sulfite was added) | 9.5 | 13.5 |
| ii) | 0.01% | 9.4 | 19.2 |
| iii) | 0.21% | 13.8 | 33.2 |
| iv) | 0.35% | 13.9 | 38.5 |
| v) | below 25 ppm | 9.6 | 13.6 |

<Stability of Batteries Containing the Electrolyte>

Batteries i) to v) are produced with the above electrolytes i) to v) and a battery casing having a size of 5 cm×9 cm×6 mm made of a laminate film having an aluminum sheet and resin layers on both sides thereof. The batteries are kept at 25° C. for one month, and then observed the appearances thereof. The results will become as shown in Table 2. It should be noted that the serial number of the battery corresponds to that of the electrolyte.

TABLE 2

| No. of battery | Apperance |
| --- | --- |
| i) | Very slight expansion is observed. |
| ii) | Very slight expansion is observed. |
| iii) | Expansion is observed. |
| iv) | Expansion is observed. |
| v) | Very slight expansion is observed. |

The refined ethylene sulfite of the invention includes a very small amount of impurities, so that it will exhibit excellent storage stability when it is added to an electrolyte for a battery.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the appended claims.

What is claimed is:

1. A method of refining raw ethylene sulfite comprising:
reacting ethylene glycol with thionyl chloride,
rectifying a material obtained by reacting ethylene glycol with thionyl chloride, and
applying further at least one process selected from the group consisting of washing with basic water, dehydration by refluxing, distillation and absorption.

2. A method for producing ethylene sulfite as set forth in claim 1, wherein said method further comprises a simple distillation process of said raw ethylene sulfite or rectified ethylene sulfite which is conducted before said refining process.

3. A method for producing ethylene sulfite as set forth in claim 1, wherein said absorbing process employs at least one absorbent selected from the group consisting of complex metal oxide, activated carbon and metal oxide.

4. A method of refining raw ethylene sulfite comprising:
reacting ethylene glycol with thionyl chloride,
applying a material obtained by reacting ethylene glycol with thionyl chloride, with at least one process selected from the group consisting of washing with basic water, dehydration by refluxing, distillation, and absorption, and
rectifying further a material thus obtained.

5. A method for producing ethylene sulfite as set forth in claim 4, wherein said method further comprises a simple distillation process of said raw ethylene sulfite or rectified ethylene sulfite which is conducted before said refining process.

6. A method for producing ethylene sulfite as set forth in claim 4, wherein said absorbing process employs at least one absorbent selected from the group consisting of complex metal oxide, activated carbon and metal oxide.

* * * * *